(12) United States Patent
Rathod et al.

(10) Patent No.: US 8,247,558 B2
(45) Date of Patent: Aug. 21, 2012

(54) PROCESS FOR THE PREPARATION OF CLOPIDOGREL AND ITS PHARMACEUTICALLY ACCEPTABLE SALTS

(75) Inventors: Parendn Dhirajlal Rathod, Gurgaon (IN); Satish Kumar Aryan, Kurukshetra (IN); Ram Chander Aryan, New Delhi (IN); Chandra Has Khanduri, Gurgaon (IN)

(73) Assignee: Ranbaxy Laboratories Limited, New Delhi (IN)

( * ) Notice: Subject to any disclaimer, the term of this patent is extended or adjusted under 35 U.S.C. 154(b) by 417 days.

(21) Appl. No.: 12/439,642

(22) PCT Filed: Sep. 4, 2007

(86) PCT No.: PCT/IB2007/053562
§ 371 (c)(1),
(2), (4) Date: Sep. 10, 2009

(87) PCT Pub. No.: WO2008/029350
PCT Pub. Date: Mar. 13, 2008

(65) Prior Publication Data
US 2010/0016594 A1 Jan. 21, 2010

(30) Foreign Application Priority Data
Sep. 4, 2006 (IN) .......................... 1971/DEL/2006

(51) Int. Cl.
*C07D 495/04* (2006.01)

(52) U.S. Cl. ....................................................... 546/114
(58) Field of Classification Search .................. 546/114
See application file for complete search history.

(56) References Cited

U.S. PATENT DOCUMENTS

| 4,529,596 | A | 7/1985 | Aubert et al. |
|---|---|---|---|
| 4,847,265 | A | 7/1989 | Badorc et al. |
| 5,132,425 | A | 7/1992 | Sotoya et al. |
| 5,189,170 | A | 2/1993 | Bouisset et al. |
| 5,204,469 | A | 4/1993 | Descamps et al. |
| 6,495,691 | B1 | 12/2002 | Horne et al. |
| 6,504,030 | B1 | 1/2003 | Bousquet et al. |
| 6,635,763 | B2 | 10/2003 | Pandey et al. |
| 2005/0059696 | A1 | 3/2005 | Reddy et al. |

FOREIGN PATENT DOCUMENTS

| WO | WO 98/51689 | 11/1998 |
|---|---|---|
| WO | WO 2004/013147 | 2/2004 |
| WO | WO 2004/074215 | 9/2004 |

*Primary Examiner* — Patrica Morris

(57) ABSTRACT

The present invention provides a process for the preparation of clopidogrel and its pharmaceutically acceptable salts thereof comprises the resolving racemic methyl alpha-5-(4,5,6,7-tetrahydro[3,2-c]thienopyridyl)(2-chlorophenyl)-acetate by the salt formation of methyl alpha-5-(4,5,6,7-tetrahydro[3,2-c]thienopyridyl)(2-chlorophenyl)-acetate with excess levorotatory camphor-10-sulfonic acid to get a maximum yield of camphor sulphonate salt of methyl S-(+)-alpha-5-(4,5,6,7-tetrahydro[3,2-c]thienopyridyl) (2-chlorophenyl)-acetate and transforming the camphor sulphonate salt to clopidogrel or its pharmaceutically acceptable salts thereof.

13 Claims, No Drawings

PROCESS FOR THE PREPARATION OF CLOPIDOGREL AND ITS PHARMACEUTICALLY ACCEPTABLE SALTS

FIELD OF THE INVENTION

The present invention provides a process for the preparation of clopidogrel and pharmaceutically acceptable salts thereof comprising resolving racemic methyl alpha-5-(4,5,6,7-tetrahydro[3,2-c]thienopyridyl)(2-chlorophenyl)-acetate by salt formation of methyl alpha-5-(4,5,6,7-tetrahydro[3,2-c]thienopyridyl)(2-chlorophenyl)-acetate with excess levorotatory camphor-10-sulfonic acid to get a maximum yield of camphor sulphonate salt of methyl S-(+)-alpha-5-(4,5,6,7-tetrahydro[3,2-c]thienopyridyl)(2-chlorophenyl)-acetate and transforming the camphor sulphonate salt to clopidogrel or pharmaceutically acceptable salts thereof.

BACKGROUND OF THE INVENTION

Clopidogrel, an inhibitor of induced platelet aggregation, is the dextro-rotatory enantiomer of methyl-alpha-5-(4,5,6,7-tetrahydro[3,2-c]thienopyridyl)-(2-chlorophenyl)-acetate, having the absolute configuration S and is represented by Formula (I).

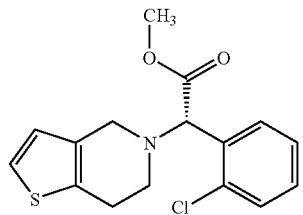

Formula I

U.S. Pat. No. 4,529,596 provides Methyl alpha-5-(4,5,6,7-tetrahydro[3,2-c]thienopyridyl)(2-chlorophenyl)-acetate.

U.S. Pat. No. 4,847,265 (herein after "the '265 patent") provides the dextro-rotatory enantiomer of methyl alpha-5-(4,5,6,7-tetrahydro(3,2-c)thienopyridyl)(2-chlorophenyl)-acetate and a pharmaceutically acceptable salts thereof. The hydrochloride, hydrogen sulfate, hydrobromide and taurocholate salts are specifically provided.

The '265 patent provides a process to obtain salts of methyl S-(+)-alpha-5-(4,5,6,7-tetrahydro[3,2-c]thienopyridyl)(2-chlorophenyl)-acetate, wherein racemic methyl-alpha-(2-chlorophenyl)-6,7-dihydro-thieno[3,2-c]pyridine-5(4H)-acetate (Formula II) is resolved by 0.399 mole equivalent of laevorotatory camphor-10-sulfonic acid monohydrate (with respect to methyl alpha-5-(4,5,6,7-tetrahydro(3,2-c)thienopyridyl)(2-chlorophenyl)-acetate) to give methyl (R)-(–)-alpha-(2-chlorophenyl)-6,7-dihydro-thieno[3,2-c]pyridine-5(4H)-acetate camphor sulfonic acid salt (Formula IV), which remains in the mother liquor and can be converted in to methyl (R)-(–)-alpha-(2-chlorophenyl)-6,7-dihydro-thieno[3,2-c]pyridine-5(4H)-acetate by known methods, whereupon methyl (S)-(+)-alpha-(2-chlorophenyl)-6,7-dihydro-thieno[3,2-c]pyridine-5(4H)-acetate camphor sulfonic acid salt (Formula III) separates out after a long period of crystallisation (72 hours) as a solid in very low yield [55% w/w and 31.94%] as shown in Scheme 1.

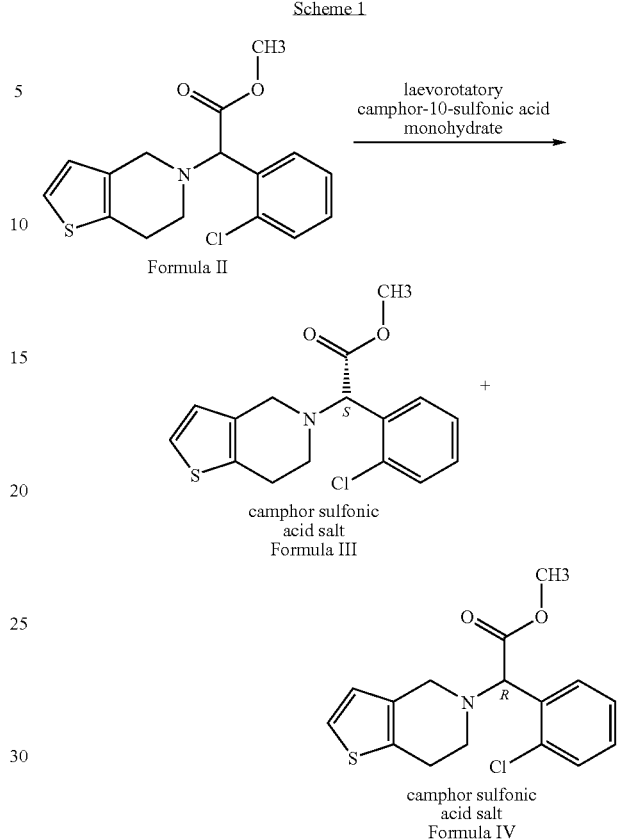

Scheme 1

Formula II camphor sulfonic acid salt
Formula III camphor sulfonic acid salt
Formula IV PCT Patent Publication No. WO 98/51689 provides the process of resolving methyl alpha-5-(4,5,6,7-tetrahydro[3,2-c]thienopyridyl)(2-chlorophenyl)-acetate in example 22 by using 0.39 mole equivalent of laevorotatory camphor-10-sulfonic acid monohydrate (with respect to methyl alpha-5-(4,5,6,7-tetrahydro[3,2-c]thienopyridyl)(2-chlorophenyl)-acetate) whereupon methyl (S)-(+)-alpha-(2-chlorophenyl)-6,7-dihydro-thieno[3,2-c]pyridine-5(4H)-acetate camphor sulfonic acid salt (Formula III) separates out after a long period of crystallisation (72 hours) as a solid in 88% yield, which is not possible even theoretically as the process involves the use of only 0.39 mole equivalent of laevorotatory camphor-10-sulfonic acid monohydrate with respect to methyl alpha-5-(4,5,6,7-tetrahydro[3,2-c]thienopyridyl)(2-chlorophenyl)-acetate.

PCT Patent Publication No. WO 2004/013147 provides a process of resolving methyl alpha-5-(4,5,6,7-tetrahydro[3,2-c]thienopyridyl)(2-chlorophenyl)-acetate by using 0.6 mole equivalent to 0.8 mole equivalent of laevorotatory camphor-10-sulfonic acid (with respect to methyl alpha-5-(4,5,6,7-tetrahydro[3,2-c]thienopyridyl)(2-chlorophenyl)-acetate). However, the patent does not provide the yield of methyl (S)-(+)-alpha-(2-chlorophenyl) -6,7-dihydro-thieno[3,2-c]pyridine-5(4H)-acetate camphor sulfonic acid salt.

U.S. Pat. No. 6,504,030 provides a process of resolving methyl alpha-5-(4,5,6,7-tetrahydro[3,2-c]thienopyridyl)(2-chlorophenyl)-acetate by using 0.6 mole equivalent of laevorotatory camphor-10-sulfonic acid (with respect to methyl alpha-5-(4,5,6,7-tetrahydro[3,2-c]thienopyridyl)(2-chlorophenyl)-acetate), whereupon methyl (S)-(+)-alpha-(2-chlorophenyl)-6,7-dihydro-thieno[3,2-c]pyridine-5(4H)-acetate camphor sulfonic acid salt (Formula III) separates out as a solid in 33% yield by crystallisation. However, the patent does not describe the time of crystallisation.

U.S. Pat. No. 6,635,763 provides a process of resolving methyl alpha-5-(4,5,6,7-tetrahydro[3,2-c]thienopyridyl)(2-chlorophenyl)-acetate in example 54, by using 1 mole equivalent of laevorotatory camphor-10-sulfonic acid (with respect to methyl alpha-5-(4,5,6,7-tetrahydro[3,2-c]thienopyridyl)(2-chlorophenyl)-acetate), whereupon methyl (S)-(+)-alpha-(2-chlorophenyl)-6,7-dihydro-thieno[3,2-c]pyridine-5(4H)-acetate camphor sulfonic acid salt (III) separates out as a solid in 36% yield by crystallisation. However, the patent does not provide the time required for crystallisation.

U.S. Patent Application No. 2005/059696 provides the process of resolving methyl alpha-5-(4,5,6,7-tetrahydro[3,2-c]thienopyridyl)(2-chlorophenyl)-acetate in example 7 by using 1 mole equivalent of laevorotatory camphor-10-sulfonic acid (with respect to methyl alpha-5-(4,5,6,7-tetrahydro[3,2-c]thienopyridyl)(2-chlorophenyl)-acetate), whereupon methyl (S)-(+)-alpha-(2-chlorophenyl)-6,7-dihydro-thieno[3,2-c]pyridine-5(4H)-acetate camphor sulfonic acid salt (III) separates out as a solid in 30.23% yield by crystallisation for 20 hours.

The problem with the preparation of clopidogrel and its pharmaceutically acceptable salts thereof is the low yield obtained in the step of resolving methyl alpha-5-(4,5,6,7-tetrahydro[3,2-c]thienopyridyl)(2-chlorophenyl)-acetate by the salt formation with levorotatory camphor-10-sulfonic acid, which increases the overall production cost of clopidogrel and its pharmaceutically acceptable salts thereof.

Accordingly, an inexpensive and commercially viable process to prepare clopidogrel and pharmaceutically acceptable salts thereof is required.

SUMMARY OF THE INVENTION

The present invention provides a process for the preparation of clopidogrel and pharmaceutically acceptable salts thereof comprising resolving racemic methyl alpha-5-(4,5,6,7-tetrahydro[3,2-c]thienopyridyl)(2-chlorophenyl)-acetate by salt formation of methyl alpha-5-(4,5,6,7-tetrahydro[3,2-c]thienopyridyl)(2-chlorophenyl)-acetate with excess levorotatory camphor-10-sulfonic acid followed by its stereoselective crystallisation to get a maximum yield of camphor sulphonate salt of methyl S-(+)-alpha-5-(4,5,6,7-tetrahydro[3,2-c]thienopyridyl)(2-chlorophenyl)-acetate and transforming the camphor sulphonate salt to clopidogrel or pharmaceutically acceptable salts thereof.

DETAILED DESCRIPTION OF THE INVENTION

A first aspect of the present invention provides a process for the preparation of clopidogrel and pharmaceutically acceptable salts thereof comprising:
 a) contacting methyl alpha-5-(4,5,6,7-tetrahydro[3,2-c]thienopyridyl)(2-chlorophenyl)-acetate with excess levorotatory camphor-10-sulfonic acid,
 b) isolating camphor sulphonate salt of methyl S-(+)-alpha-5-(4,5,6,7-tetrahydro[3,2-c]thienopyridyl)(2-chlorophenyl)-acetate,
 c) transforming the camphor sulphonate salt of methyl S-(+)-alpha-5-(4,5,6,7-tetrahydro[3,2-c]thienopyridyl)(2-chlorophenyl)-acetate into clopidogrel or pharmaceutically acceptable salts thereof.

Racemic Methyl alpha-5-(4,5,6,7-tetrahydro[3,2-c]thienopyridyl)(2-chlorophenyl)-acetate may be obtained by any of the methods known in the art including those described in U.S. Pat. Nos. 4,529,596; 5,132,435; 5,189,170; 5,204,469; 6,495,691; and 6,635,763, which are incorporated herein by reference.

The racemic methyl alpha-5-(4,5,6,7-tetrahydro[3,2-c]thienopyridyl)(2-chlorophenyl)-acetate may be taken as a solution. The solution of methyl alpha-5-(4,5,6,7-tetrahydro[3,2-c]thienopyridyl)(2-chlorophenyl)-acetate may be obtained by dissolving methyl alpha-5-(4,5,6,7-tetrahydro[3,2-c]thienopyridyl)(2-chlorophenyl)-acetate in an organic solvent.

The solvent used for the dissolution of methyl alpha-5-(4,5,6,7-tetrahydro[3,2-c]thienopyridyl)(2-chlorophenyl)-acetate include chlorinated hydrocarbons, alcohols, ketones, alkyl acetates, alkyl nitrites and mixture(s) thereof.

Racemic methyl alpha-5-(4,5,6,7-tetrahydro[3,2-c]thienopyridyl)(2-chlorophenyl)-acetate and laevorotatory camphor-10-sulfonic acid may be taken in a molar ratio of 1:1.1 to 1:1.5.

The solution obtained in step a) may be stirred at a temperature of about 20-35° C. Preferably it may be stirred at about 25° C.

The solution obtained in step a) may be stirred for about 48 hours to about 72 hours. Preferably it may be stirred for about 48 hours.

The solution obtained in step a) after stirring may be cooled at a temperature in the range of 0 to 5° C. and may be stirred for 30 minutes to 1 hour.

The isolation of camphor sulphonate salt of methyl S-(+)-alpha-5-(4,5,6,7-tetrahydro[3,2-c]thienopyridyl)(2-chlorophenyl)-acetate may be accomplished by cooling, filtration, centrifugation or a combination thereof.

The isolated camphor sulphonate salt of methyl S-(+)-alpha-5-(4,5,6,7-tetrahydro[3,2-c]thienopyridyl)(2-chlorophenyl)-acetate may be dried under reduced pressure at temperatures in the range of about 30 to about 50° C. for about 10 hours to about 24 hours.

The camphor sulphonate salt of methyl S-(+)-alpha-5-(4,5,6,7-tetrahydro[3,2-c]thienopyridyl)(2-chlorophenyl)-acetate may be converted into clopidogrel or pharmaceutically acceptable salts thereof by conventional methods such as by the treatment of camphor sulphonate salt of methyl S-(+)-alpha-5-(4,5,6,7-tetrahydro[3,2-c]thienopyridyl)(2-chlorophenyl)-acetate with a base in a suitable organic solvent under stirring at a temperature in the range of about 0° C. to about 30° C.

The base used for the liberation of clopidogrel may include sodium hydroxide, potassium hydroxide, sodium bicarbonate or potassium bicarbonate, sodium carbonate, and potassium carbonate. The base may be taken as an aqueous solution.

Pharmaceutically acceptable salts of clopidogrel include salts of clopidogrel base with acetic acid, benzoic acid, fumaric acid, benzoic acid, maleic acid, citric acid, tartaric acid, methanesulfonic acid, ethanesulfonic acid, benzenesulfonic acid, p-toluene sulfonic acid, hydrochloric acid, hydrobromic acid and sulfuric acid.

Pharmaceutically acceptable salts of clopidogrel may be prepared by treating clopidogrel base with a corresponding acid in a suitable solvent.

Examples of suitable organic solvent include chlorinated hydrocarbons, alkyl acetates, ketones, ethers and mixture(s) thereof.

Chlorinated hydrocarbons may be selected from the group consisting of dichloromethane, dichloroethane, trichloroethane, tetrachloroethane, dichloropropane, chloroform, carbon tetrachloride and mixture(s) thereof.

Alcohols may be selected from the group comprising of methanol, ethanol, n-propanol, 2-propanol, n-butanol, 2-butanol and mixture(s) thereof.

Alkyl nitriles may be selected from the group comprising of acetonitrile, propionitrile and mixture(s) thereof.

Alkyl acetate may be selected from the group consisting of ethyl acetate, n-propyl acetate, isopropyl acetate, n-butyl acetate, isobutyl acetate and mixture(s) thereof.

Ketones may be selected from the group consisting of acetone, methyl ethyl ketone, methyl isobutyl ketone and mixture(s) thereof.

Ethers may be selected from the group consisting of diethyl ether, diisopropyl ether, tert-butyl methyl ether, dioxane, tetrahydrofuran and mixture(s) thereof.

Clopidogrel base may be treated with acid at a temperature in the range of about 0 to about 35° C.

While the present invention has been described in terms of its specific embodiments, certain modifications and equivalents will be apparent to those skilled in the art and are intended to be included within the scope of the present invention.

EXAMPLES

Example 1

Preparation of Methyl Alpha-5-(4,5,6,7-Tetrahydro [3,2-C]Thienopyridyl)(2-Chlorophenyl)-Acetate 4,5,6,7-tetrahydrothieno[3,2-c]pyridine hydrochloride (1 kg) was dissolved in methanol (5 liter) and treated sequentially with sodium bicarbonate (1.43 kg) and methyl 2-chloro-o-chlorophenyl acetate (1.5 kg) at 25-30° C. The solution was heated to 65° C. and stirred for 24 hours. The reaction mixture was cooled to 25° C., filtered and concentrated under vacuum. The residue was dissolved in dichloromethane (10 liter) and washed four times with water (5 liter each time). Organic layer was concentrated under reduced pressure to afford methyl alpha-5-(4,5,6,7-tetrahydro[3,2-c]thienopyridyl)(2-chlorophenyl)-acetate as an oily product.

Yield: 1.75 kg.

Example 2

Preparation of Camphor Sulphonate Salt of Clopidogrel

Methyl alpha-5-(4,5,6,7-tetrahydro[3,2-c]thienopyridyl)(2-chlorophenyl)-acetate (1 kg) obtained from example 1 was diluted with acetone (2500 ml) and treated with 1R-10-camphor sulphonic acid (794 g). The reaction mixture was stirred for 48 hours at 25° C. The reaction mixture was cooled to 0° C. and stirred for 30 minutes. The crystals obtained were filtered, washed with chilled acetone (1 liter, 0° C.) and dried under reduced pressure at 45° C. for 15 hours.

Yield: 860 g (49.93%)
Purity: 98.32% (By HPLC).
Chiral purity: 1.5% R isomer.

Example 3

Preparation of Clopidogrel (R)-Camphor sulphonate salt of clopidogrel (100 g) obtained from example 2 was dissolved in dichloromethane (600 ml) at 25-30° C. and 5% sodium bicarbonate solution (400 ml) was added dropwise in 30 minutes at 0-5° C. The resulting reaction mixture was stirred for 30 minutes at 0-5° C. The organic layer was separated, washed three times with water (200 ml each time) and concentrated under reduced pressure at 30° C. to afford clopidogrel as an oily product.

Yield: 57.6 g (99.2%)
Purity: 99.21% (By HPLC).
Chiral purity: R isomer 0.64%.

Example 4

Preparation of Clopidogrel Salt

A: Preparation of Clopidogrel Hydrobromide Salt

Clopidogrel (10 g) obtained from example 3 was dissolved in diisopropyl ether (129.3 ml) at 25-30° C. and 47% aqueous hydrobromic acid solution (3.79 ml) was added dropwise in 30 minutes at 25-30° C. The resulting suspension was stirred for 3 hours at 25-30° C. The resulting crude solid was filtered, washed with diisopropyl ether (10 ml) at 25-30° C. and dried under reduced pressure at 30-35° C. for 15 hours.

Yield: 12 g

The crude solid (5 g) was added in a mixture of isopropanol (56 ml) and diisopropyl ether (37.3 ml) at 25-30° C. The resulting suspension was heated to 65° C. and then cooled to 25-30° C. in 1 hour. Resulting solution was stirred for 15 hours at 25-30° C. and then again cooled to 0° C. and stirred for 30 minutes at the same temperature. Resulting solid was filtered, washed with a mixture of isopropanol (3 ml) and diisopropyl ether (2 ml) and dried under reduced pressure at 45° C.

Yield: 3.2 g
Purity: 99.7% (By HPLC).
Chiral purity: R isomer nil.

B: Preparation of Clopidogrel Bisulfate Salt

Clopidogrel (10 g) obtained from example 3 was dissolved in acetone (43 ml) at 5-10° C. and concentrated sulfuric acid (1.78 ml) was added dropwise in 10 minutes at 5-10° C. The resulting solution was stirred for 1 hour at 5-10° C. The resulting solid was filtered and dried under reduced pressure at 50° C. for 5 hours.

Yield: 11 g
Purity: 99.42% (By HPLC).
Chiral purity: R isomer nil.

The invention claimed is:

1. A process for the preparation of clopidogrel and pharmaceutically acceptable salts thereof comprising:
   a) contacting methyl alpha-5-4,5,6,7-tetrahydro[3,2-c]thienopyridyl)(2-chlorophenyl)-acetate with levorotatory camphor-10-sulfonic acid wherein methyl alpha-5-(4,5,6,7-tetrahydro[3,2-c]thienopyridyl)2-chlorophenyl)-acetate and levorotatory camphor-10-sulfonic acid is taken in the mole ratio of at least 1:1.1,
   b) isolating camphor sulphonate salt of methyl S-(+)-alpha-5-(4,5,6,7-tetrahydro[3,2-c]thienopyridyl)(2-chlorophenyl)-acetate,
   c) transforming the camphor sulphonate salt of methyl S-(+)-alpha-5-4,5,6,7-tetrahydro[3,2-c]thienopyridyl)(2-chlorophenyl)acetate into clopidogrel or pharmaceutically acceptable salts thereof.

2. A process according to claim 1, wherein methyl alpha-5-(4,5,6,7-tetrahydro[3,2-c]thienopyridyl)(2-chlorophenyl)-acetate and levorotatory camphor-10-sulfonic acid are taken in a molar ratio of 1:1.1 to 1:1.5.

3. A process according to claim 1, wherein the isolation of camphor sulphonate salt of methyl S-(+)-alpha-5-(4,5,6,7- tetrahydro[3,2-c]thienopyridyl)(2-chlorophenyl)-acetate is accomplished by cooling, filtration, centrifugation or a combination thereof.

4. A process according to claim 1, wherein isolated camphor sulphonate salt of methyl S-(+)-alpha-5-(4,5,6,7-tetrahydro[3,2-c]thienopyridyl)(2-chlorophenyl)-acetate is dried under reduced pressure at temperatures in the range of 30 to 50° C.

5. A process according to claim 4, wherein isolated camphor sulphonate salt of methyl S-(+)-alpha-5-(4,5,6,7-tetrahydro[3,2-c]thienopyridyl)(2-chlorophenylacetate is dried for 10 hours to 24 hours.

6. A process according to claim 1, wherein camphor sulphonate salt of methyl S-(+)-alpha-5-(4,5,6,7-tetrahydro[3,2-c]thienopyridyl)(2-chlorophenyl)acetate is converted into clopidogrel or pharmaceutically acceptable salts thereof by the treatment of camphor sulphonate salt of methyl S-(+)-alpha-5-4,5,6,7-tetrahydro[3,2-c]thienopyridyl)(2-chlorophenyl)-acetate with a base in an organic solvent.

7. A process according to claim 6, wherein base is selected from the group consisting of sodium hydroxide, potassium hydroxide, sodium bicarbonate, potassium bicarbonate, sodium carbonate and potassium carbonate.

8. A process according to claim 6, wherein the suitable organic solvent is selected from the group consisting of chlorinated hydrocarbons, alkyl acetates, ketones, ethers and mixture(s) thereof.

9. A process according to claim 8, wherein the chlorinated hydrocarbon is selected from the group consisting of dichloromethane, dichloroethane, trichloroethane, tetrachloroethane, dichloropropane, chloroform, carbon tetrachloride and mixture(s) thereof.

10. A process according to claim 8, wherein the alkyl acetate is selected from the group consisting of ethyl acetate, n-propyl acetate, isopropyl acetate, n-butyl acetate, isobutyl acetate and mixture(s) thereof.

11. A process according to claim 8, wherein the ketone is selected from the group consisting of acetone, methyl ethyl ketone, methyl isobutyl ketone and mixture(s) thereof.

12. A process according to claim 8, wherein the ether is selected from the group consisting of diethyl ether, diisopropyl ether, tert-butyl methyl ether, dioxane, tetrahydrofuran and mixture(s) thereof.

13. A process according to claim 1, wherein the pharmaceutically acceptable salts of clopidogrel is prepared by treating clopidogrel with an acid in a solvent.

* * * * *

UNITED STATES PATENT AND TRADEMARK OFFICE
CERTIFICATE OF CORRECTION

| | | |
|---|---|---|
| PATENT NO. | : 8,247,558 B2 | Page 1 of 1 |
| APPLICATION NO. | : 12/439642 | |
| DATED | : August 21, 2012 | |
| INVENTOR(S) | : Parendu Dhirajlal Rathod | |

It is certified that error appears in the above-identified patent and that said Letters Patent is hereby corrected as shown below:

On the title page:
    Item (75), Inventor Parendn Dhirajlal Rathod should read --Parendu Dhirajlal Rathod--

In the Specifications:

Column 4, line 14:
    change nitrites to --nitriles--

In the Claims:

Column 6, Claim 1, line 49:
    change alpha-5-4,5,6,7-tetrahydro[3,2-c] to --alpha-5-(4,5,6,7-tetrahydro[3,2-c]--

Column 7, Claim 6, line 18:
    change alpha-5-4,5,6,7-tetrahydro[3,2-c] to --alpha-5-(4,5,6,7-tetrahydro[3,2-c]--

Signed and Sealed this
Twenty-third Day of July, 2013

Teresa Stanek Rea
*Acting Director of the United States Patent and Trademark Office*